United States Patent

Steiger et al.

[11] Patent Number: 6,071,259
[45] Date of Patent: Jun. 6, 2000

[54] OPTIONAL INSERTER FOR DIGITAL TAMPONS

[75] Inventors: Fred H. Steiger, East Brunswick; Philip J. Stevenson, Princeton; Dennis C. Holtman, Flemington, all of N.J.

[73] Assignee: McNeil-PPC, Inc., Skillman, N.J.

[21] Appl. No.: 08/969,223

[22] Filed: Nov. 13, 1997

Related U.S. Application Data

[63] Continuation-in-part of application No. 08/810,102, Mar. 3, 1997, which is a continuation-in-part of application No. 08/365,657, Dec. 29, 1994.

[51] Int. Cl.⁷ .................................................. A61F 13/20
[52] U.S. Cl. .................................................................. 604/11
[58] Field of Search ............................. 604/1, 11, 904

[56] References Cited

U.S. PATENT DOCUMENTS

| | | | |
|---|---|---|---|
| 2,355,917 | 8/1944 | Knight | 128/263 |
| 3,998,225 | 12/1976 | Hytonen | 604/11 |
| 4,027,673 | 6/1977 | Poncy et al. | 604/369 |
| 4,573,964 | 3/1986 | Huffman | 604/11 |

FOREIGN PATENT DOCUMENTS

| | | | |
|---|---|---|---|
| 614475 | 2/1961 | Canada | 604/904 |
| 882807 | 6/1943 | France . | |
| 2620684 | 3/1989 | France | 604/904 |
| 26 17 642 | 11/1977 | Germany . | |
| 375102 | 3/1964 | Switzerland . | |
| 519197 | 3/1940 | United Kingdom | 604/1 |
| 710670 | 6/1954 | United Kingdom | 604/904 |

*Primary Examiner*—Michael J. Milano

[57] ABSTRACT

A tampon inserter is included in a package of about the size used for conventional digital tampons, without, a decrease in the number of such tampons in the package. The inserter provides an alternate means for insertion of digital and other tampons and may be used as a training device for new users.

7 Claims, 3 Drawing Sheets

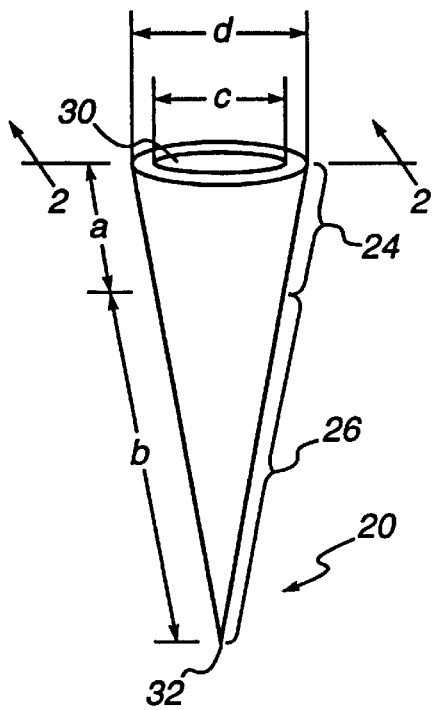
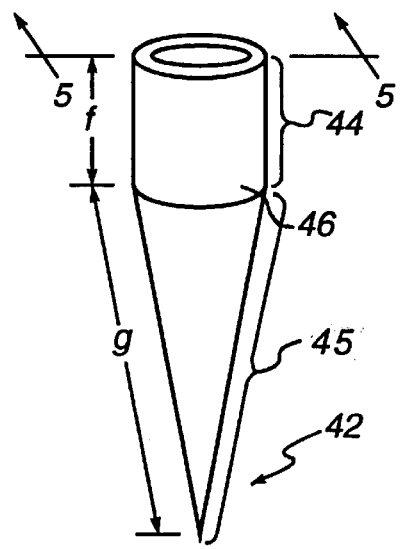
FIG. 1
FIG. 4
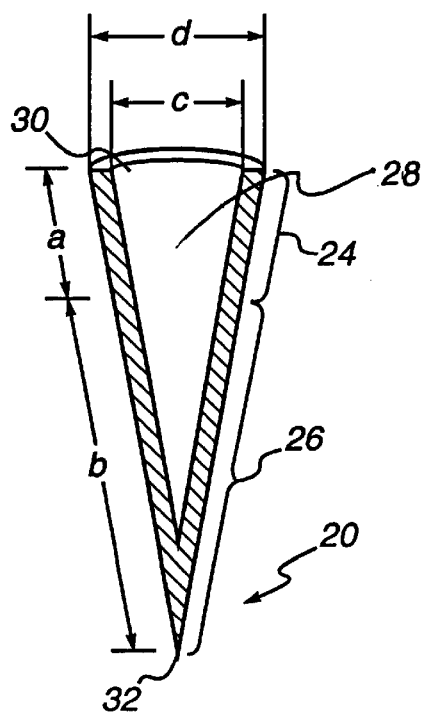
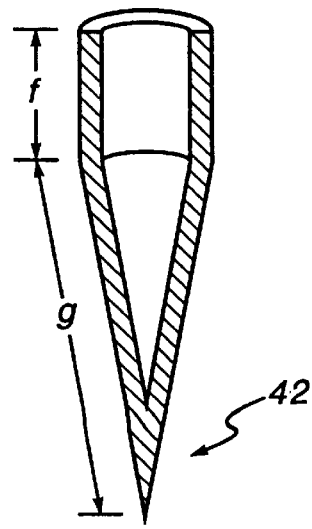
FIG. 2
FIG. 5

OPTIONAL INSERTER FOR DIGITAL TAMPONS

This is a continuation of application Ser. No. 08/810,102, filed Mar. 3, 1997, which is a Continuation application of Ser. No. 08/365,657, filed Dec. 29, 1994 now abandoned.

BACKGROUND OF THE INVENTION

This invention relates to inserters for tampons, and, more specifically, to inserters for use with digital tampons, capable of being packaged with such tampons without a substantial increase in the size of the packaging or a decrease in the number of tampons in the package.

Women now have a variety of options with respect to the types of tampons they may use. These options have been created, in part, to satisfy the preferences of individuals. For example, some women prefer digital (hand inserted) tampons because of the relatively small packages in which they are contained. These smaller packages tend to be more convenient for compact storage and discreet personal transport. The digital tampon is also appreciated because of the degree of control which can be exercised in inserting the product. Another group of women prefers applicator tampons or the use of some type of a device which assists in the manual placement of tampons. This preference is typically based on a need to satisfy sanitary concerns. For some women, it may also be based on ease of insertion with the use of a separate device. Despite these distinct preferences, there are some women who have no preference and will use the tampon which is most readily available (or least expensive). There are also times when a woman who prefers the digital may have a need or desire to use an inserting device (i.e., when she is concerned about soiling her hands or clothes). There are also times when the regular user of an inserter would prefer to use, or at least would not be averse to using, a digital tampon.

The term "inserter" is used herein to mean any device used to assist in the manual placement of a tampon, including, but not limited to, conventional and unique applicators, and stick-type inserters (discussed in more detail below). The term "user" is used herein to mean the person in whose body the tampon is placed, and, where appropriate, the person who physically inserts the tampon (who may be another individual). "Digital tampons" is used herein to mean any tampon which is ordinarily inserted by hand without the use of an inserter. The "advanced end" of the tampon is the portion of the tampon which first enters the vagina of a user; the "trailing end" is the portion of the tampon which is last to enter the vagina, typically the end to which the tampon's withdrawal string is attached. The trailing end, is typically the last or the only portion of the tampon which comes in contact with an inserter.

The choice for women between the use of a digital tampon and a tampon which employs, by necessity, an inserter, is often made at the time tampons are purchased. Conventional tampons are packaged either with or without inserters. That is, either the woman purchases and uses a package of tampons with inserters or purchases and uses a package of digital tampons. If a woman wants the option of using inserters or refraining from doing so, she typically has to purchase one of each type of tampon (i.e., a package of digital tampons and a package of tampons with inserters). This purchasing option has obvious disadvantages both economically and logistically (e.g., the woman would need to open both packages and thereafter use the tampons as desired).

To expand the user's options, digital tampons could be packaged with inserters. Using conventional digital tampons and conventional inserters, however, this arrangement typically requires that the packaging either be substantially increased in size or include fewer tampons. If the inserters are large, unsightly or both, women who use digital tampons alone on a regular basis may look with disfavor on the packaging. The perception that the additional inserters, which may not be used on a regular basis, add substantially to the total cost of the packaged tampons, may also alienate potential users. To save space, the digital tampons could possibly be packaged inside of the inserters. However, there is typically a tight frictional fit between the inner surface of conventional inserters and the outer surface of the enclosed tampons. Thus, with conventional products (e.g. a tampon inside a conventional applicator), considerable effort would be needed to remove the tampon from within an inserter sized and configured to eject the tampon directly into the body of a user. See, for example, U.S. Pat. Nos. 2,355,628, 2,335,917 and 3,543,754, which disclose tampons ejected from inserters.

It would appear that the disadvantage discussed above (i.e., increased package size and/or fewer tampons per package) could be overcome to some extent by the use of stick-type inserters. Such inserters are disclosed in, for example, U.S. Pat. No. 3,983,875. Although such stick-type inserters may be packaged with digital tampons without a substantial increase in the size of the packaging or a substantial decrease in the number of tampons it contains, stick-type inserters have other disadvantages. For instance, tampons used with stick-type inserters, must be relatively harder than conventional digital tampons, at least in the area where the tampon comes into contact with the inserter. If the inserter is not hard enough, the manipulation of the tampon by the stick-type inserter is problematic. When the tampon is made harder to guard against the problems associated with the use of a stick-type inserter, the resulting tampon, as compared to a typical digital tampon, may not expand rapidly enough to prevent leakage around the tampon prior to its softening and becoming effective. Stick-type inserters also have a threatening appearance and may cause injury if employed improperly (factors which also weigh against user satisfaction).

It is therefore a general object of this invention to provide women with the option of inserting tampons either with or without inserters.

Another object of this invention is to give the user the option of buying a package containing digital tampons and inserters, with little or no increase in the size of the package or decrease in the number of tampons therein.

An additional object of this invention is to provide inserters which the user may employ to avoid soiling her fingers or undue microbial contamination of her perineal area, while requiring for insertion no significant increase in effort on the part of the user.

The foregoing specific objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

SUMMARY OF THE INVENTION

With the above objectives in mind, the present invention provides, in general, a device for inserting a tampon, comprising a tube with a first section and a second section, the first section preferably comprising a chamber with an open end. In the preferred embodiment, the open end is sized to receive the trailing end of the tampon and the chamber is sized to accommodate a desired portion of that trailing end as the tampon is placed in the device and advanced to a desired position within the vaginal cavity of a user. The second section is sized and configured to be held by hand during the insertion of the tampon. At the option of the user, the tampon may be of the kind which may be inserted digitally. The packaging of inserters and tampons together gives the user the option of digital or device-assisted insertion.

Those skilled in the art will appreciate that it is highly desirable that the edges of the inserter be prevented from contacting (and thereby possibly abrading) the vaginal wall. To this end, it is desirable that the trailing end of the tampon be compressed when the tampon is held by the inserter, and that the cross-section of the tampon other than at the compressed trailing edge be larger than the outer cross-section of the inserter.

In various embodiments of the present invention, the device includes, by way of example, (1) a cone-shaped tube in which the first section comprises an open end and the second section extends to a point distal from the open end, (2) a cone-shaped tube where the open end of the first section comprises a parallel-walled collar, (3) a cylindrical tube where the first section comprises a parallel-walled collar and the second section is fluted, (4) a tube sized and configured to house a tampon within the second section, ready for use, and to accommodate the tampon in the first section during insertion, and (5) other tubes sized and configured in accordance with the invention.

It is preferred that the inserter be sized to be packaged with tampons so that there need be a minimal, if any, increase in the overall size of the packaging over packaging for tampons alone. It is also preferred that the surface of the device be configured to avoid or at least minimize abrasive contact with the vaginal wall during insertion and upon its withdrawal after the tampon is in the desired position. Furthermore, it is preferred that the second section of the inserter be of a length which would allow the user to hold the inserter at a desirable point away from the user's body.

In its preferred form, the present invention may be produced on a continuous production line wherein each individual device is subsequently cut and formed as desired or produced by other conventional manufacturing means known to those skilled in the art.

BRIEF DESCRIPTION OF THE DRAWINGS

There are seen in the drawings forms of the present invention which are preferred and which are the best mode presently contemplated for carrying out the invention. It should be understood, however, that the invention is not limited to the precise arrangements and instrumentalities shown.

FIG. 1 is a perspective view of one embodiment of an inserter device in accordance with the present invention.

FIG. 2 is a cross-sectional view, taken along the line 2—2 in FIG. 1.

FIG. 4 is a perspective view of another embodiment of an inserter device in accordance with the present invention.

FIG. 5 is a cross-sectional view, taken along the line 5—5 in FIG. 4.

DETAILED DESCRIPTION

Figure 3:
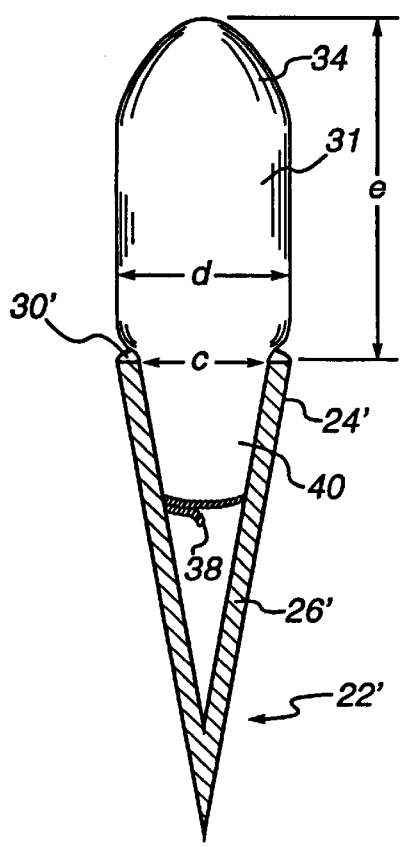
FIG. 3 is a perspective view, partly in cross-section, showing a tampon positioned in one embodiment of an inserter device in accordance with the present invention.

Referring now to the drawings in detail, wherein like reference numerals indicate like elements, there is seen in FIGS. 1 and 2 an inserter in accordance with the present invention, designated generally by the reference numeral 20. The inserter 20 comprises a conical tube 22 with a first section 24 and a second section 26.

Preferably, inserter 20 is made of a degradable material, such as paper or degradable plastic, although those skilled in the art will realize that a number of suitable materials may be used. For instance, inserter 20 may be made from molded plastic, although rolled cardboard would be ecologically more acceptable and thus, preferable. It is also preferred that the surface of tube 20 be configured, composed, or coated to minimize abrasive contact with the vaginal wall during insertion and upon its withdrawal after the tampon is in the desired operative position. In this embodiment, in which the tube 22 is cone-shaped, the angle of taper of the second section 26 in the region of the apex 32, the thickness of the wall of inserter 20, and the cross-section of the space, or chamber 28, within tube 22 (see FIG. 2), are all variable and dependent upon, among other things, the type and nature of the material used, the size and configuration of the tampon with which inserter 20 is to be used, the manufacturing process employed to produce inserter 20, the desired size and configuration of the package in which inserter 20 will be provided to the user and the number and size of the tampons to be packaged therewith. The invention may be produced, as will occur to those skilled in the art, by a number of manufacturing methods including, but not limited to, continuous production line processes in which each individual device is cut and formed as desired.

First section 24, which includes the chamber 28 and open end 30, is the portion of inserter 20 which comes into contact with and frictionally holds the tampon during insertion. The size, configuration and geometric shape of chamber 28 and open end 30 are dependent upon, among other things, the portion of the tampon which must be held by inserter 20 to complete the insertion step. Length "a", which is the distance along the inside of chamber 28 which ordinarily comes into contact with the tampon during insertion, is preferably of a dimension to allow the section of the tampon in chamber 28 to slip out of inserter 20 after the tampon is in the desired operative position within the vagina of a user. Thus, length "a" is dependent on, among others, such factors as the frictional resistance between chamber 28 and the trailing end of the tampon, and the shape of the trailing end. The resistance is dependent on, among other things, the material used for the inserter 20, any surface coatings or texture the inner wall of the chamber 27 may have, and on the texture of the trailing end where it comes into contact with inner wall of the chamber 28.

The open end 30 is sized and configured to receive the trailing end of a tampon. For instance, referring now to FIGS. 1, 2 and 3, in a preferred embodiment of the present invention, inner cross-section "c" of open end 30 (FIGS. 1 and 2) is less than the maximum cross-section of the tampon (seen in FIG. 3 and designated generally by the reference numeral 31) and the outer cross-section "d" of open end 30 is no greater and preferably, smaller than the maximum cross-section of the tampon 31. It will be understood that digital tampons of the type referred to here are packaged in a compressed initial state, and quickly expand after insertion and in the presence of moisture. The above-mentioned relative dimensions relate to the tampon 31 in its initial state, as it is inserted for use. With the above-described configuration of the inserter 20, as best seen in FIG. 3, tampon 31, when positioned in first section 24, and with a withdrawal string 38 attached to its trailing end, extends away from open end 30 by a distance equal to distance "e" between the advanced end 34 of tampon 31 and the location 36 on tampon 31 where, moving from trailing end 40 toward advanced end 34, the cross-section of tampon 31 first exceeds the inner cross-section "c" of open end 30. One skilled in the art would realize that distance "c" may be reduced and more of trailing end 40 may be disposed within the chamber 28, depending on the material in trailing end 40 and the force used to place trailing end 40 in the chamber 28.

Tampons 31 of the kinds referred to here are typically about 9 to 15 mm. in diameter and about 5 cm in length in their packaged and initial state. Inserter 20 for use with such tampons 31 are typically and preferably in the range of about 2½ to 3 inches in length, and in view of consideration of ease of manipulation and convenience of packaging, generally not in excess of 4 inches in length.

In the embodiment shown in FIGS. 1, 2 and 3, the second section 26 of the inserter 20 comprises the remainder of the tube 22 including the apex 32. One skilled in the art would realize that the second section 26 may be tapered or otherwise configured for more comfortable use of inserter 20. It is preferred that second section 26 be held by hand during the insertion of the tampon and be of a sufficient length to allow the user to hold the tube 22 at a desirable distance from the vagina. One of ordinary skill in the art would realize that length "b" is dependent to some extent on the type and nature of the material used for the tube 22, the size and configuration of the tampon 31 with which the tube 22 is used, the manufacturing process employed to produce the tube 22, and the size and configuration of the package in which inserters 20 are to be supplied to the user. The distance is dependent upon the distance "a" and the surface required for the user to comfortably handle the inserter 20 by grasping the second section 26.

Referring now to FIGS. 4 and 5, there is seen another embodiment of the invention. In this embodiment, an inserter, designated generally by the reference numeral 42, has a first section 44, which consists of a parallel-walled collar 46. The collar 46 has a length "f". A second section 45, similar to the above-described second section 26 of the inserter 20, includes a cone-shaped body of a length "g".

This embodiment of the invention operates in a manner similar to the embodiment in FIGS. 1, 2 and 3 (and described above), but is capable of holding tampons more securely while not substantially increasing the package size needed for inserter 42 and tampons.

Like the embodiment in FIGS. 1, 2, and 3, the inserter 42 is "nestable" for packaging purposes, as will be explained below in relation to FIG. 10.

Figure 6:
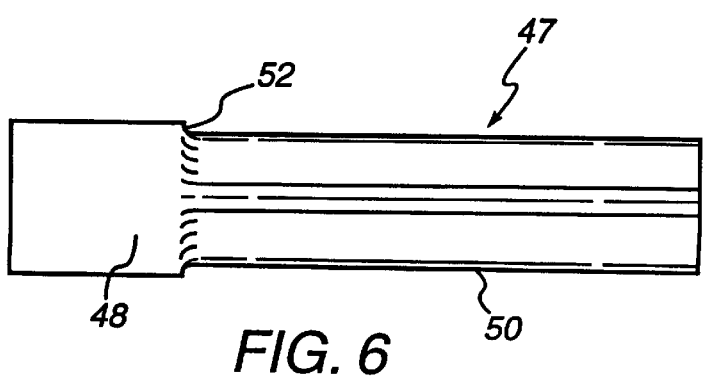
FIG. 6 is a side elevation view of another embodiment of an inserter device in accordance with the present invention.
Figure 7:
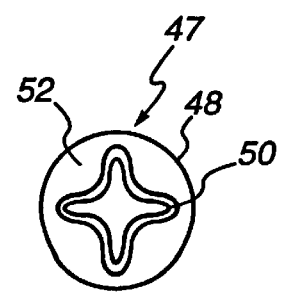
FIG. 7 is an end elevation view of the embodiment shown in FIG. 6.

In still another embodiment of the invention, seen in FIGS. 6 and 7, an inserter 47 includes first section 48 and a second section 50, swaged to a reduced cross-section. While operating similarly to the inserter depicted in FIG. 1, the inserter 47 can be made most economically by a continuous process, for instance, by cutting lengths from a continuous rolled paper tube having an inner diameter sufficient to hold a tampon. The second section 50 meets the first section 48 at a necked down transition portion 52. The "fluted" cross-section of the second section 50 (FIG. 7) reinforces and rigidifies the second section 50, while enabling the first section 48 to act as a natural receptacle for a tampon.

Figure 8:
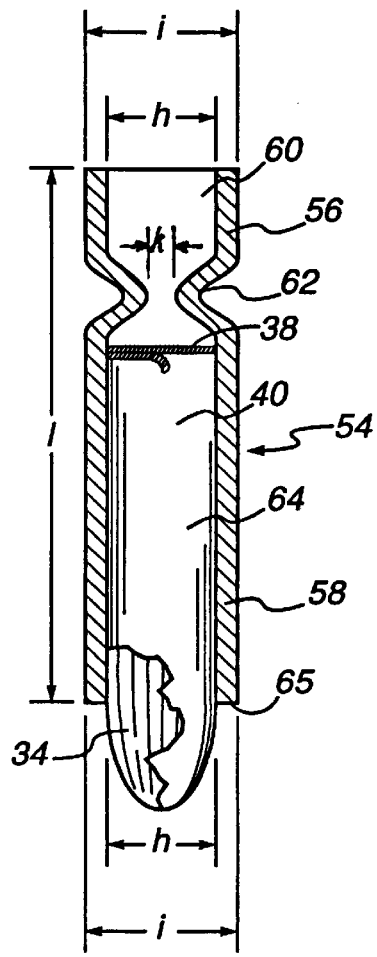
FIG. 8 is a cross-sectional view, in side elevation, of another embodiment of an inserter device in accordance with the present invention.

Referring now to FIG. 8 there is seen an inserter designated generally by the reference numeral 54, which includes a first section 56 and a second section 58. In this embodiment, the inserter 54 may be constructed from a continuous rolled paper tube with an inner cross-section "h" and an outer cross-section "i", an open end 60 and a zone 62 of reduced cross-section "k". Preferably, the cross-section "h" and length "l" of the second section 58 are sufficient to enable the second section 58 to hold a wrapped tampon 64. It is preferred that the distance "l" from the zone 62 to the open end 65 of the first section 56 be of a length sufficient to hold the trailing end 66 the tampon 64 during insertion. See in this regard FIG. 9.

Figure 9:
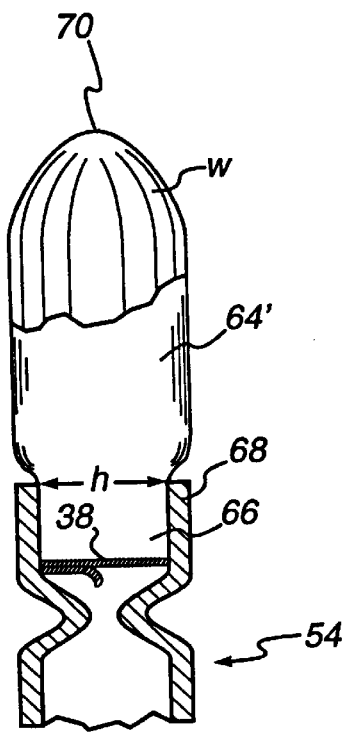
FIG. 9 is a side elevation view of a tampon in accordance with the present invention.

Referring now to FIG. 9, it will be seen that the interior of the first section 56 of the inserter 54 defines a chamber 68 configured to receive the compressed trailing end 66 of a tampon 64'. Compression of the trailing end 66 of the tampon 64' causes a desired frictional engagement between the trailing end 66 and the inserter 54. The user can choose to insert the tampon 64' digitally, or to use an inserter, such as the inserter 54. It will be recognized that by unwrapping only the trailing end of the tampon 64' and placing the unwrapped trailing end 66 of a tampon 64' in an inserter 54 while grasping the advanced end 70 still in its wrapper "w", the user need not touch the actual surface of tampon 64' before insertion.

Figure 10:
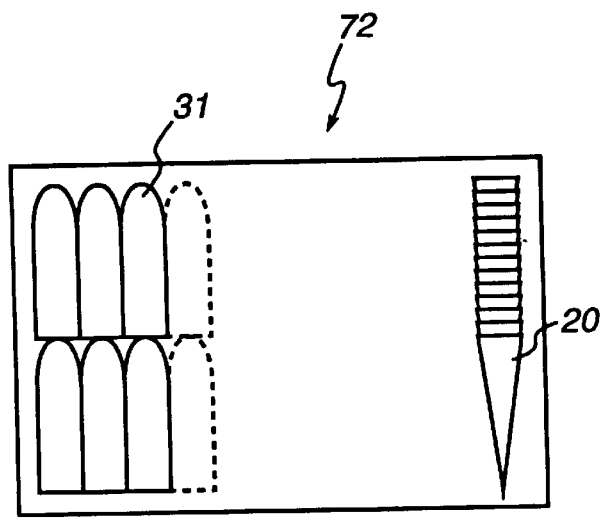
FIG. 10 is a side elevation view, in cross-section, of a package containing inserters of the type shown in FIGS. 1, 2 and 3 and tampons of the type shown in FIG. 9.
Figure 11:
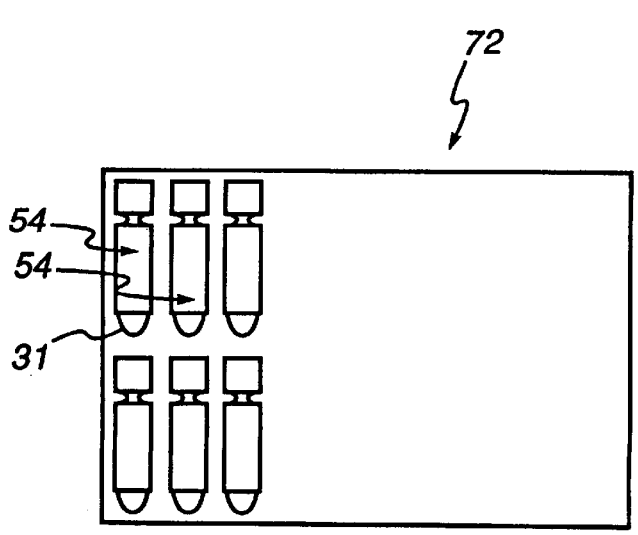
FIG. 11 is a side elevation view, in cross-section, of a package containing inserters of the type shown in FIG. 8 and tampons of the type shown in FIG. 9.
Figure 12:
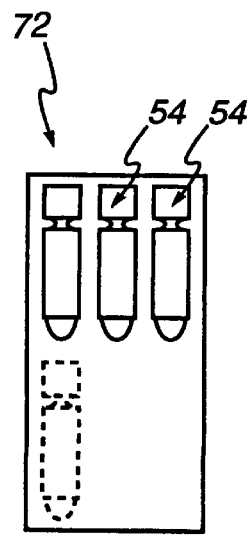
FIG. 12 is an end elevation view of the package shown in FIG. 11.

Referring now to FIGS. 10, 11, and 12 the manner in which tampons and inserters may be packaged in accordance with the invention is illustrated. It will be seen in FIG. 10 that inserters 20, in a number equal to the number of digital tampons 31, contained in the package (the package being designated by the reference numeral 72), are provided within the package. The inserters 20 are nested together for compactness. Other forms of inserters, such as the inserters 42, may also be nested in the illustrated manner. It will be appreciated that the inserters 20 need add little, if anything, to the overall volume of the package 72.

In the case of inserters such as the inserters 54, seen in FIGS. 8 and 9 tampons 31 may themselves conveniently be nested within the second sections 58 of inserters. This relationship is depicted in FIG. 8, and a package 72 containing such tampons 31 and inserters 54 as seen in FIGS. 11 and 12. Inserters such as those seen in FIGS. 6 and 7 are preferably sized to be packaged in groups with tampons, so that there need be little, if any, increase in the overall size of a package to accommodate the inserters.

The present invention, including the inserters and tampons, or the inserters alone, may readily be employed in training new tampon users.

The above embodiments are merely illustrations of the apparatus claimed herein. The invention also includes other embodiments not specifically disclosed above, embodiments which one skilled in the art would realize and envision as equivalents or derivations of the embodiments shown and existing in other specific forms without departing from its spirit or essential attributes. Numerous variations may be made within the scope of this invention without departing from the principle of the invention and without sacrificing its chief advantages. Thus, the terms and expressions have been used as terms of description and not terms of limitation. Reference should be made to the appended claims, rather than to the foregoing specification and drawings, as indicating the scope of the invention.

We claim:

1. Tampon and apparatus for inserting said tampon, comprising,
    a tampon having an advanced end and a trailing end, and which may selectively be inserted digitally;
    an inserter having a first section and a second section;
        said first section comprising a chamber with an open end, said chamber sized and configured to accommodate only a portion of said trailing end, said trailing end capable of being held in said chamber while said advanced end of said tampon projects from said open end of said chamber as said tampon is advanced during insertion to an operative disposition within a user's vagina; and
        said second section sized and configured to be held by hand during the insertion of the tampon;
    wherein a portion of said trailing end of said tampon is held within said chamber, and wherein said inserter is a hollow cone having a tapering inner cross-section, said first section comprising the base of the cone, whereby movement of said tampon into said inserter is limited by the taper of the inner cross-section of said inserter from said first section to said second section.

2. Tampon and apparatus in accordance with claim 1, wherein said tampon has a maximum cross-section and said open end of said first section has an inner and an outer cross-section, said inner cross-section being smaller in cross-section than the maximum cross-section of the tampon and said outer cross-section being no greater than the maximum cross-section of the tampon.

3. Tampon and apparatus in accordance with claim 2, wherein said chamber comprises a cylindrical collar, one end of said collar defining said open end of said chamber.

4. Tampon and apparatus in accordance with claim 1 wherein said inserter is so configured that a plurality of said inserters are nestable.

5. Tampon and apparatus in accordance with claim 1, wherein the surface of said inserter is configured to minimize abrasive contact with the vagina during insertion of said tampon and apparatus where said tampon is positioned in said chamber and upon withdrawal of said apparatus after said tampon has been operatively disposed in the vagina.

6. Tampon and apparatus in accordance with claim 5, wherein said tampon has a maximum cross-section and said open end of said first section has an inner and an outer cross-section, said inner cross-section being smaller in cross-section than the maximum cross-section of the tampon and said outer cross-section being no greater than the maximum cross-section of the tampon.

7. Tampon and apparatus in accordance with claim 1, wherein said second section is of a length sufficient to allow a user to hold said inserter at a point spaced from the user's vagina during insertion.

* * * * *